(12) United States Patent
Schaffer et al.

(10) Patent No.: US 12,404,632 B2
(45) Date of Patent: Sep. 2, 2025

(54) HIGH STRENGTH WIRE

(71) Applicant: Fort Wayne Metals Research Products, LLC, Fort Wayne, IN (US)

(72) Inventors: Jeremy E. Schaffer, Fort Wayne, IN (US); Robert A. Mitchell, Huntington, IN (US); Andrew Kritsch, Fort Wayne, IN (US)

(73) Assignee: Fort Wayne Metals Research Products, LLC, Fort Wayne, IN (US)

( * ) Notice: Subject to any disclaimer, the term of this patent is extended or adjusted under 35 U.S.C. 154(b) by 255 days.

(21) Appl. No.: 18/019,348

(22) PCT Filed: Aug. 3, 2021

(86) PCT No.: PCT/US2021/044395
§ 371 (c)(1),
(2) Date: Feb. 2, 2023

(87) PCT Pub. No.: WO2022/031740
PCT Pub. Date: Feb. 10, 2022

(65) Prior Publication Data
US 2023/0272578 A1    Aug. 31, 2023

Related U.S. Application Data

(60) Provisional application No. 63/060,417, filed on Aug. 3, 2020.

(51) Int. Cl.
*D07B 1/06*    (2006.01)

(52) U.S. Cl.
CPC ........... *D07B 1/068* (2013.01); *D07B 1/0686* (2013.01); *D07B 2201/2009* (2013.01); *D07B 2205/3082* (2013.01); *D07B 2205/3085* (2013.01)

(58) Field of Classification Search
CPC .... D07B 1/0673; D07B 1/068; D07B 1/0686; D07B 2201/2009; D07B 2205/3082;
(Continued)

(56) References Cited

U.S. PATENT DOCUMENTS

2018/0289375 A1* 10/2018 Hebert ............... A61B 17/1215
2020/0070583 A1    3/2020 Shibata et al.

FOREIGN PATENT DOCUMENTS

| JP | 4659972 B2 * | 3/2011 | |
| WO | 2018183862 A1 | 10/2018 | |
| WO | WO-2020150023 A1 * | 7/2020 | ......... A61B 17/0057 |

OTHER PUBLICATIONS

Extended European Search Report received for corresponding European Patent Application No. 21854655.4, dated Aug. 20, 2024 10 pages.
(Continued)

*Primary Examiner* — Shaun R Hurley
(74) *Attorney, Agent, or Firm* — Faegre Drinker Biddle & Reath LLP

(57) ABSTRACT

Ultra-High-Strength (UHS) wires are suited to high strength wire, strands, cables and rope applications including robotics force transmission and other high-performance mono- and multifilament wire applications. The wires exhibit high strength, low stretch and fatigue durability. Exemplary UHS materials include binary molybdenum-rhenium or tungsten-rhenium alloys with between 20 and 50 wt. % rhenium. These alloys are processed from a moderate strength (<2 GPa) warm-drawn rod to drawn monofilament wire with extreme nanocrystalline grain refinement, high apparent fatigue durability, and ultimate strength levels exceeding 5 GPa in all cases, and up to 6.8 GPa at monofilament diameters ranging from 7 to 100 μm.

23 Claims, 12 Drawing Sheets

(58) Field of Classification Search
CPC .... D07B 2205/3085; D07B 2501/2046; A61B 1/0057
See application file for complete search history.

(56) References Cited

OTHER PUBLICATIONS

"Evaluation of properties and special features for high-temperature applications of rhenium" Research Articale from AOP conference Proceedings, dated Jan. 15, 1992, 15 pages.

* cited by examiner

HIGH STRENGTH WIRE

CROSS REFERENCE TO RELATED APPLICATION

This application claims the benefit of U.S. Provisional Patent Application No. 63/060,417 filed Aug. 3, 2020 and entitled HIGH STRENGTH WIRE, the entire disclosure of which is incorporated herein by reference.

BACKGROUND

1. Technical Field

The present disclosure relates to high-strength wire alloys.

2. Description of the Related Art

Over the past half-century, high strength fine wires have been employed in a wide variety of applications, ranging from rotorcraft torsion-tension strap-laminates to vascular interventional devices. Typically, these wires have diameters less than 150 μm and ultimate strengths up to about 3 to 3.4 GPa.

The tire cord industry offers examples of higher strengths, but without the corrosion resistance required in medical devices. For example, strength levels of up to 5.5 GPa are achieved in bulk production of 100-200 μm moderate-alloy, heavily cold-worked, steel wire. One particular known alloy is 0.96% C-0.2% Si-0.3% Mn-0.2% Cr (balance Fe), which was processed to a diameter of 40 μm achieving an ultimate tensile strength of 5.7 GPa. Other known alloys are made from heavily drawn mild steel with ferritic, bainitic and/or fine pearlitic compositions that possess negative corrosion-rest-potentials on the order of −600 to −400 mV in approx. 0.9% sodium chloride against a saturated calumel standard, and must be protected from the effects of even mild saline corrosion environments. While these materials exhibit high strength, a material with far superior corrosion resistance is required for medical applications.

What is needed is an improvement over the foregoing.

SUMMARY

The present disclosure provides wires made of tungsten-rhenium and molybdenum-rhenium that have been subject to novel processing to create deeply cold-worked, smoothly finished, fine wire. The result is a very strong fiber with much higher strength than any known polycrystalline metal and far greater corrosion resistance than ultra-high strength steel fibers developed to date.

In one form thereof, the present disclosure provides a high strength cable construct including a plurality of drawn alloy filaments formed from one of a tungsten-rhenium or a molybdenum-rhenium alloy, wherein the cable construct exhibits strength reaching 4800 N/mm$^2$, the strength calculated using a solid cross-sectional filament area as the area and a break load of the cable.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION

Figure 1:
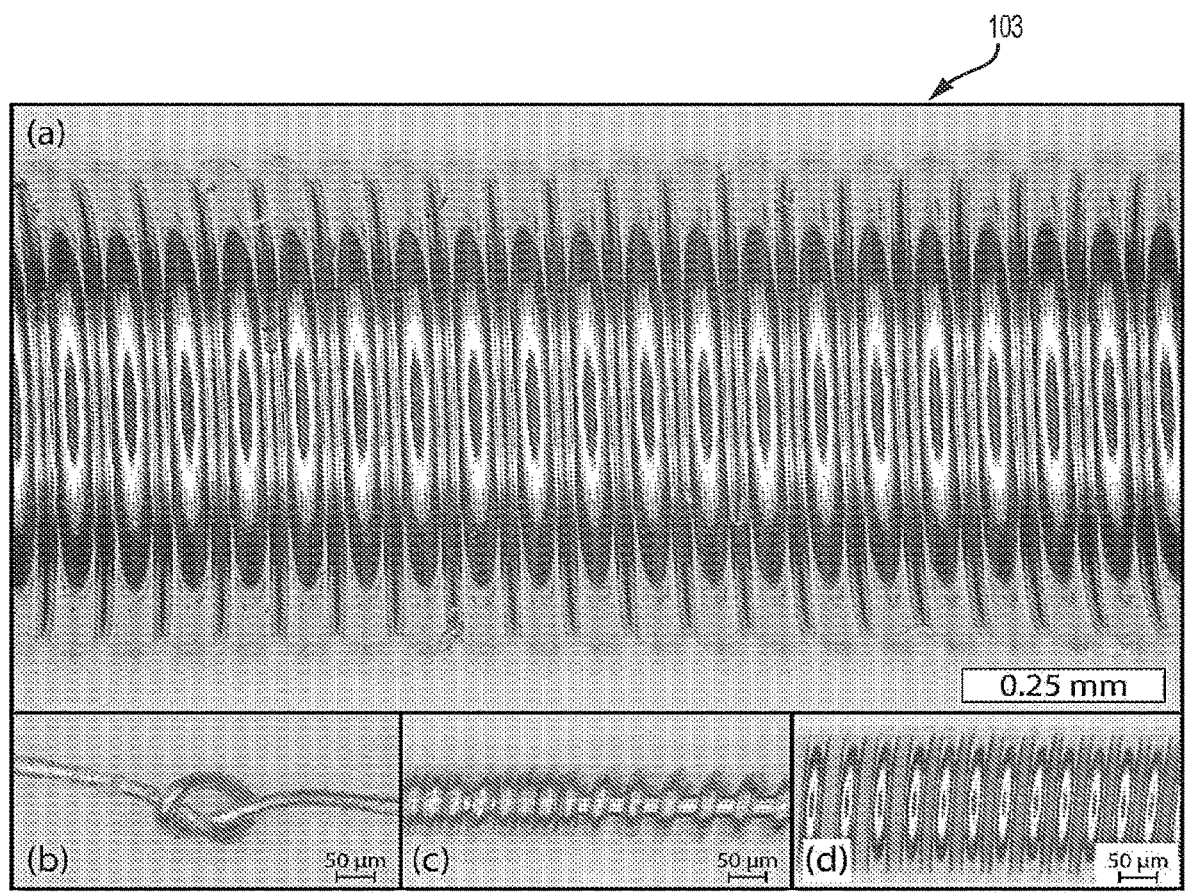
FIG. 1(a) shows a formed 71 μm Mo47Re wire drawn to an ultimate strength level of 5.1 GPa and coiled to an outside diameter of 0.65 mm, drawn to scale according to the 0.25 mm scale shown at lower right.
FIG. 1(b) shows a formed fine drawn 25 μm Mo41Re wire drawn to an ultimate strength level of 5.6 GPa knotted to a surface strain exceeding 30%, drawn to scale according to the 50 μm scale shown at lower right.
FIG. 1(c) shows a formed wire the same as the wire shown in FIG. 1(b), a self-coiled to a surface strain exceeding 40%, drawn to scale according to the 50 μm scale shown at lower right.
FIG. 1(d) shows a formed fine drawn 25 μm W26Re wire drawn to an ultimate strength level of 4.7 GPa coiled to an outside diameter of 0.18 mm, drawn to scale according to the 50 μm scale shown at lower right.

There is a performance-driven demand for ultra-high strength and high stiffness wire materials with strength levels greater than 3 GPa and even 5 GPa possessing suitably high ductility and corrosion resistance. This demand arises in applications such as high strength cable assemblies for surgical robotics, endoscopic actuation, firing, release and articulation, high strength reinforcement applications such as tire cord wire and rotorcraft torsion-tension straps, and even high strength medical device subcomponents. These applications tend to share some performance demands that translate into property requirements such as high ultimate strength, flexibility, good ductility and forming characteristics, lustrous surface finish, and/or good durability against cyclic mechanical fatigue. Many systems utilize pulleys, sheaths, or other guiding surfaces to direct the work provided by such cable. Microcables in these systems must endure tensile stresses, bending stresses and abrasion introduced by pulleys and guiding surfaces.

As described in detail below, tungsten-rhenium and molybdenum-rhenium wires and cables in accordance with the present disclosure achieve ultra-high ultimate strength levels of greater than 5 to 6 GPa, and even 6.9 GPa (1 million pounds per square inch) in mono- and multi-filament wire constructs. In exemplary embodiments wire compositions include 26 wt. % rhenium with balance tungsten and inevitable impurities ("W26Re"); 41 wt. % rhenium with balance molybdenum and inevitable impurities ("Mo41Re"); and 47.5 wt. % rhenium with balance molybdenum and inevitable impurities ("Mo47Re"). Generally speaking, rhenium content for W—Re and Mo—Re alloys can range from as little as 20, 25 or 30 wt. % to as much as 35, 40, 45 or 50 wt. %, or may be any rhenium content within any range defined by any of the foregoing values, with the balance of the alloy being either tungsten or molybdenum and inevitable impurities. Such wires are formulated and processed to achieve strength of as little as 4800 N/mm$^2$ or 5500 N/mm$^2$, and as much as 6200 N/mm$^2$, or any range of strengths defined by any of the foregoing values.

As described in further detail below, monofilament, monolithic wires 103 (FIG. 9A) are characterized with outer diameters $D_{2S}$ ranging from as little as 7 μm (0.00028 in), 10 μm, 12 μm, 20 μm or 25 μm, and up to 30 μm, 40 μm, 50 μm, 60 μm, 70 μm, 80 μm, 90 μm or 100 μm (0.00394 in) or any range of diameters within any range defined by any of the foregoing values. Wires 103 exhibit plastic forming capabilities up to 40% surface strain in flexure without apparent surface rupture or micro cracking despite ultra-high strength levels.

The present material provides superlative strength properties, apparent toughness, and ductility characteristics combined with exceptional surface hardness, rendering it suitable for use subcomponents for myriad applications. Such applications include robotics, surgical robotics, and other high-performance motion or force control hardware as described further below, where high-fidelity force transmission is married to extreme durability requirements.

Additionally, the Mo—Re and W—Re systems described and shown herein possesses corrosion rest potentials that are +400 to +600 mV more noble that their high strength steel counterparts. To the extent that this corrosion performance may be preserved in a highly stressed, cold-worked wire state as described herein, such fibers can be used in diverse additional applications such as high-performance tire reinforcement and rotorcraft tension-torsion straps.

1. Terminology

As used herein, "wire" or "wire product" encompasses continuous wire and wire products which may be continuously produced and wound onto a spool for later dispensation and use, such as wire having a round cross section and wire having a non-round cross section, including flat wire or ribbon. "Wire" or "wire product" also encompasses other wire-based products such as strands, cables, coil, and tubing, which may be produced at a particular length depending on a particular application. Although round cross-sectional wire forms are shown in the Figures of the present application and described further below, non-round wire forms may also be produced in accordance with the present disclosure. Exemplary non-round forms include polygonal cross-sectional shapes such as rectangular cross-sectional shapes.

"Fine wire" refers to a wire having an outer diameter of less than 1 mm. "Ultrafine wire" refers to a wire having an outer diameter of 50 μm or less.

"Monolithic" refers to a wire or other structure which is formed as a single piece of material.

"DFT®" is a registered trademark of Fort Wayne Metals Research Products Corp. of Fort Wayne, Ind., and refers to a bimetal or poly-metal composite wire product including two or more concentric layers of metals or alloys, typically at least one outer layer or shell disposed over a core filament, and formed by drawing a tube or multiple tube layers over a solid metallic wire core element.

"Impurities," "incidental impurities" and "trace impurities" are material constituents present in a material at less than 500 parts per million or 0.05 wt. %. Alloys "free" of or "excluding" a certain constituent are alloys having such a constituent in amounts equal to or less the 500 parts per million impurities threshold.

"Medical-grade" materials are materials suitable for use within the human body. "Medical-grade" materials specifically exclude certain materials not suitable for use in, or in connection with medical procedures on, the human body. For examples non-medical grade materials are materials not suitable for contact with tissue and/or blood, including materials which cannot pass cytotoxicity testing of at least one hour of such contact. Non-medical grade materials include heavy metals including lead and cadmium, materials such as beryllium and beryllium copper, and any other materials generally regarded as toxic to the human body or otherwise damaging to human tissue.

"OD" refers to the outside diameter of a metallic wire or other construct.

2. Exemplary Wire Constructs and Materials

Tungsten—26 wt. % rhenium (W26Re), molybdenum—41 wt. % rhenium (Mo41Re) and molybdenum—47.5 wt. % rhenium (Mo47Re) alloys were procured at diameters ranging from 1.0 to 6.0 mm. All materials were processed into an intermediate wire construct by conventional hot working, warm working and cold work finishing with varied intermediate annealing in the range of 1400 to 2000 K in either an inert argon atmosphere or under reducing conditions (pure hydrogen).

The intermediate wire constructs were cold drawn using diamond tooling with individual die reductions ranging from 8 to 25 area % to a final diameter $D_{2S}$ ranging from 7 up to 100 µm with greater than 90% retained cold work after final annealing.

Additional descriptions of cold work, wire drawing, annealing and other wire-processing methods which may be used in connection with the present materials are presented below. Further information may be found in U.S. Patent Application Publication No. WO 2019/200046 filed Apr. 11, 2019 and entitled WIRE FOR A HIGH DENSITY AND BIOSTABLE MICROELECTRODE ARRAY FOR NEURAL ELECTRODE STIMULATION AND RECORDING, the entire disclosure of which is hereby expressly incorporated herein by reference.

Assessment of surface plastic flow, malleability and ductility can be conducted by hand, such as through coiling wire 103 around a mandrel (FIGS. 1(a), 1(c) and 1(d)) or knot fabrication (FIG. 1(b)). Tensile testing can be performed using an Instron twin screw tester equipped with 10 to 1000 N load cells depending on wire size and strength level and using flat face pneumatic grips and fine emery to avoid grip slip. For strength data reported herein, monotonic axial tensile strains of the sub-100 µm wires were calculated based on cross head displacement. All wires 103 are initially produced with either a bright surface finish (FIG. 1) or a smooth oxide finish which can show blemishes, cracking or other defects upon excessive stress.

FIG. 1 shows formed wires of various compositions, described herein, exhibiting high surface plasticity and lack of apparent surface cracking despite being processed to ultimate strength levels exceeding 4.7 GPa. In FIG. 1(a), a Mo47Re wire 103 drawn to an ultimate strength level of 5.1 GPa and having an outer diameter of 71 µm is shown coiled to an overall coil diameter of 0.65 mm. As illustrated by the lustrous and low-defect appearance of the wire shown in the photograph of FIG. 1(a) illustrates that the wire 103 suffered no discernable cracking or visible degradation from the high stress imposed by the coiling.

In FIG. 1(b), a Mo41Re wire 103 drawn to an ultimate strength level of 5.6 GPa and having an outer diameter of 25 µm is shown knotted to a surface strain exceeding 30%. Once again, the lustrous and low-defect appearance of the wire shown in the photograph of FIG. 1(b) illustrates that the wire 103 suffered no discernable cracking or visible degradation from the high stress imposed by the knotting. In FIG. 1(c) the same 25 µm Mo41Re wire is shown self-coiled to a surface strain exceeding 40%, again without apparent cracking or degradation.

In FIG. 1(d) a formed fine drawn W26Re wire 103 drawn to an ultimate strength level of 4.7 GPa and having an outer diameter of 25 µm is shown coiled to an outside diameter of 0.18 mm without loss of surface luster or cracking.

As further discussed below, the wires of FIG. 1 all exhibit ultra-high strength reaching or exceeding 4.5 GPa. Some materials exhibited strength in excess of 5 GPa. Yet, none of the materials exhibited surface cracking or degradation upon coiling or knotting. Thus, even the highest strength (>5 GPa) materials remained surprisingly formable without fracture, being capable of coiling around mandrels of similar diameter to the wire 103 or pulling tight in a simple overhand knot to 30-50% surface plastic strain with no apparent surface rupture. FIG. 1(b), for example, shows inspection of coil intrados surfaces at optical magnifications up to 400 times. FIG. 1(b) demonstrates a lack of apparent microcracking or crack formation, and a preservation of the original surface luster of the wire before strain.

The wires shown in FIG. 1 and described herein were also subject to lab bench comparison to other common medical device and other high performance materials including 18-8 stainless steel, CoCr, CoNiCrMo, nitinol alloys, tungsten and tungsten alloys. As described herein, these comparisons illustrate that ultra-high strength (UHS) wire 103 made in accordance with the present disclosure can be readily formable into mono- and multifilament wire constructs including coils, cables, ropes and other formed subcomponents utilizing a plurality of wires while experiencing little or no reduction in strength. For a given geometric construction, subcomponents produced from the present UHS wires may therefore provide nearly 200% greater strength than ultra-high-strength stainless steel (3.1 GPa) or even high strength tungsten (4.1 GPa).

Figure 2:
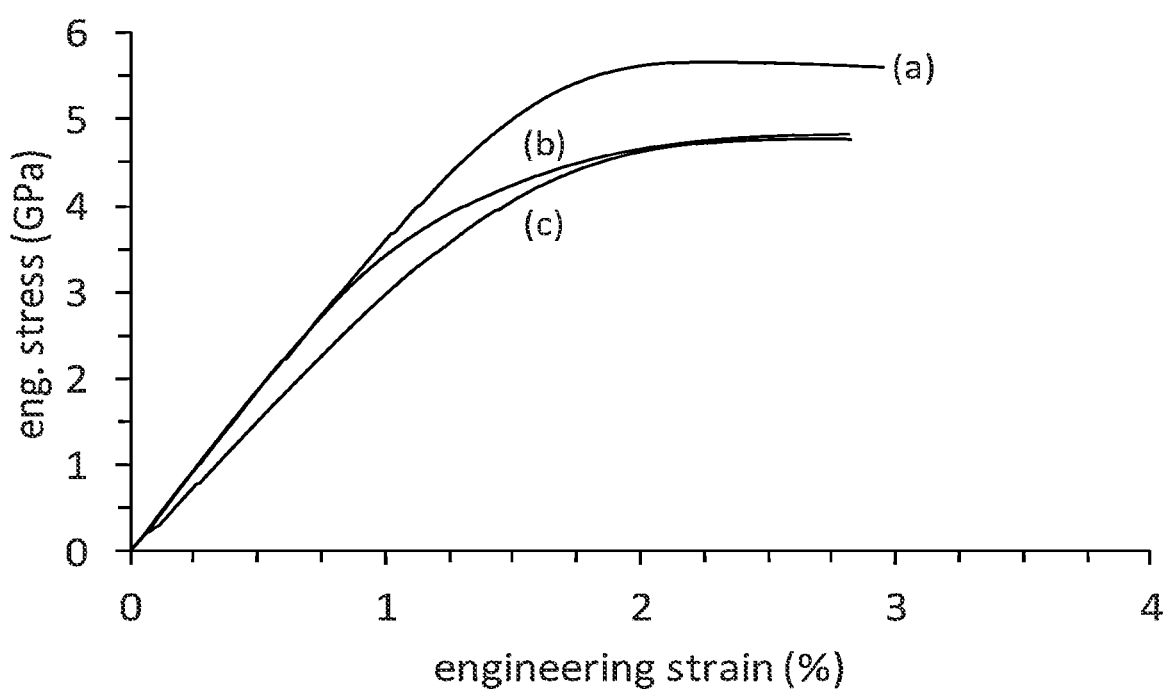
FIG. 2 is a stress-strain graph showing a room temperature (22±3° C.) monotonic axial tension test-to-failure, in which the X-axis shows stress (GPa) and the Y-axis shows engineering strain (% of original 127 mm gage length) for round wires including (a) Ø 25 μm Mo41Re; (b) Ø 25 μm W26Re, and; (c) Ø 25 μm Mo47Re.

Turning to FIG. 2, a room temperature engineering stress-strain response of 25 µm diameter Mo41Re round wire is shown at curve (a), together with a similarly processed W26Re round wire shown at curve (b) and Mo47Re round wire shown at curve (c). As illustrated, at greater than 90% cold work, all samples maintained ductile yielding with uniform elongation exceeding 2.5% and strength levels greater than 4.5 GPa. The tensile strength and elongation to fracture of the 25 µm diameter Mo41Re was the greatest at 5.66 GPa and 3% engineering strain respectively giving a specific work energy to fracture of about 120 mJ/mm³, a 0.2% yield strength of 5.00 GPa, and a measured Young's elastic modulus of 370 GPa.

Figure 3:
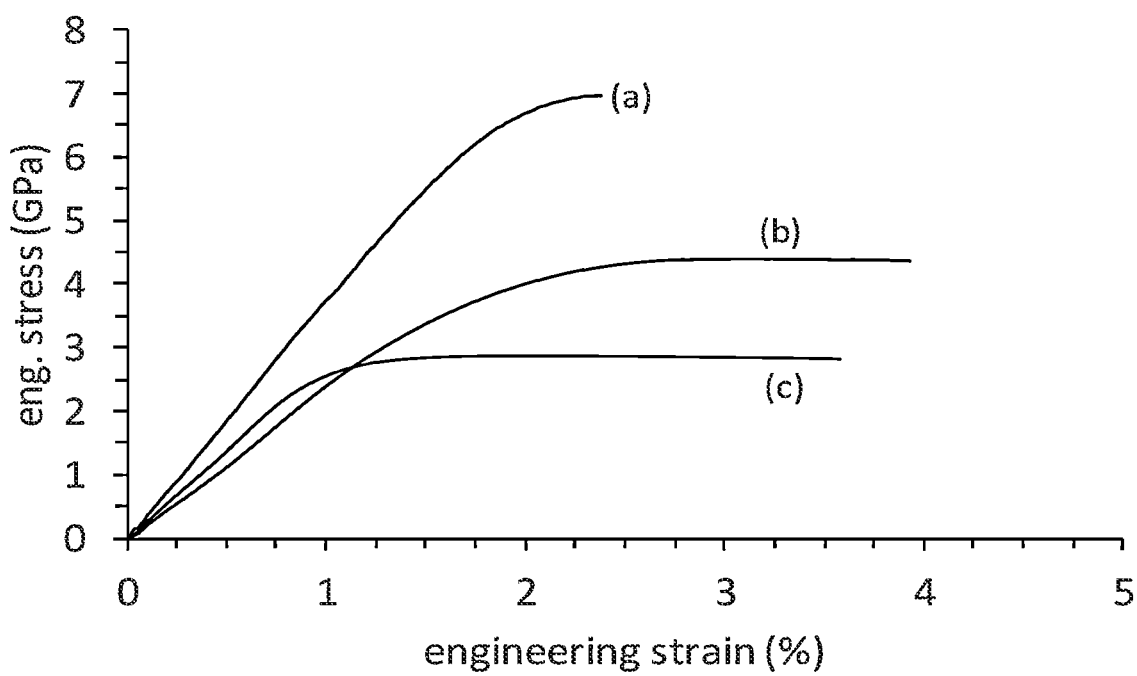
FIG. 3 is a stress-strain graph showing a room temperature (22±3° C.) monotonic axial tension test-to-failure, in which the X-axis shows stress (GPa) and the Y-axis shows engineering strain (% of original gage length) for round wires including (a) Ø 7 μm Mo41Re; (b) Ø 100 μm W26Re, and; (c) Ø 100 μm high strength drawn pure tungsten.

FIG. 3 shows a comparison in tensile behavior between a predicate high strength, warm drawn 100 µm tungsten wire, used as a control, and two wires made in accordance with the present disclosure. The predicate wire is shown at curve (c). A first wire made in accordance with the present disclosure is cold drawn 100 µm Mo41Re wire, shown at curve (b). A second wire made in accordance with the present disclosure cold drawn 7 µm Mo41Re wire, shown at curve (a).

Comparing the 100 µm samples, at room temperature, axial specific work-energy to fracture in a tensile test increased from 87 to 129 mJ/mm^3 in the UHS Mo—Re wire (curve (b)) giving an improvement in fracture energy of greater than 40% compared to drawn tungsten (curve (c)). Meanwhile, curve (a) for the Mo41Re Ø 7 µm wire provides a superlative example of ultimate tensile strength at 6.9 GPa (greater than one million pounds per square inch) with a 0.2% yield strength of 6.2 GPa, a measured Young's elastic modulus of 371 GPa, 2.3% engineering strain to fracture and a specific work energy to fracture of 99.6 mJ/mm³.

In addition, W—Re and Mo—Re materials made in accordance with the present disclosure exhibit excellent fatigue strength. To assess fatigue durability, a wire 103 is placed under alternating stress loads, whether in tension-tension, flexural or combined tension-flexural loading to define a given peak loading stress calculated at the maximal wire surface location. Fatigue is conducted in dry ambient laboratory air at −100 to 100° C. The alternating loads are repeated and the number of cycles is counted.

Wires 103 exhibit fatigue durability reaching 10 million cycles without fracture under loading stress of at least 1000 N/mm². In exemplary embodiments, wire 103 exhibit fatigue durability reaching 10 million cycles without fracture under greater loading stresses such as 1500 N/mm² or 2000 N/mm².

3. Cable Constructs

Referring now to FIGS. 4-8C, Exemplary applications of wire 103 include multifilament cable constructions such as cable 10. For purposes of the present disclosure, cable 10 may be expressed as [A]×[B] where [A] is the number of elements in the cable, and [B] is the number of filaments per element. This basic construct can be used to express additional cable constructions, such as [A]×[B]×[C] where [C] is a number of [A]×[B] cables used to create the finished construct. Additional cable constructs based on these general principles of expression can be specified using additional algebraic formulations, as noted in Table 1 below.

By way of example, FIG. 1 shows a "37×7" cable 10 including four radial layers, including a first, central or core layer 16 having a single strand 12, a second layer 18 including six strands 12 which surround the first layer 16, a third layer 20 including twelve strands 12 which surround the second layer 18, and a fourth or outer layer 22 including eighteen strands 12 which surround the third layer 20. With the addition of each successive layer, a separate wire construct is formed within the larger construct of cable 10. For example, core layer 16 is a "1×7" wire construct because it is a single strand 12 of seven filaments 14. Second layer 18, when combined with core layer 16, can be considered a "7×7" wire construct because it has seven strands 12 each having seven filaments. In similar fashion, third layer 20 combines with layers 16 and 18 to form a "19×7" construct and outer layer 22 combines with layers 16, 18 and 20 to form a "37×7" construct. By the same token, a "1×19" wire construct is the same as core layer 16, but with 19 filaments integrated into the strand 12. "7×19," "19×19," and "37×19" constructs can be made by adding layers 18, 20 and 22 respectively using strands 12 each having 19 filaments. Cable 10, or any cable in accordance with the present disclosure, may be formed by integrating wires 103 as the filaments 14 of the cable.

Figure 7:
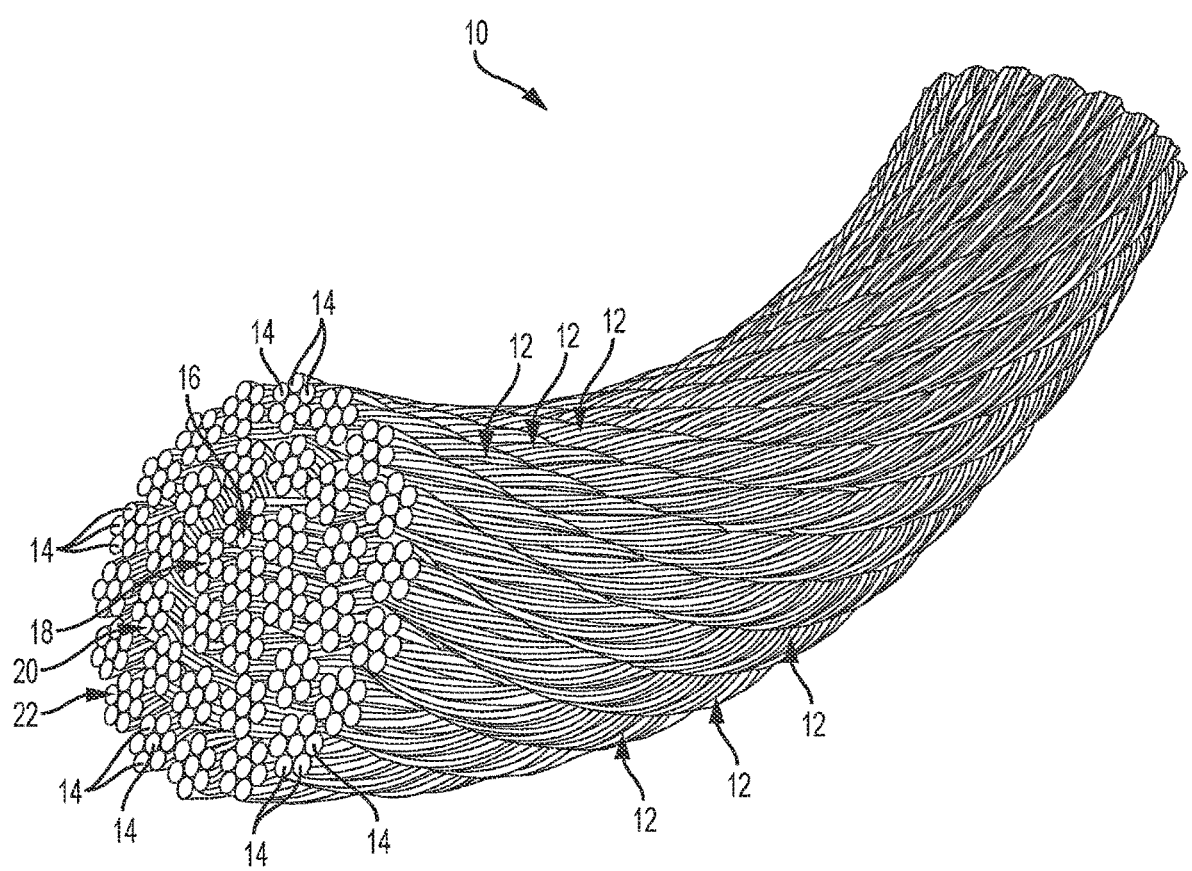
FIG. 7 is a cross-section, perspective view of the cable assembly shown in FIG. 6.
Figure 8A:
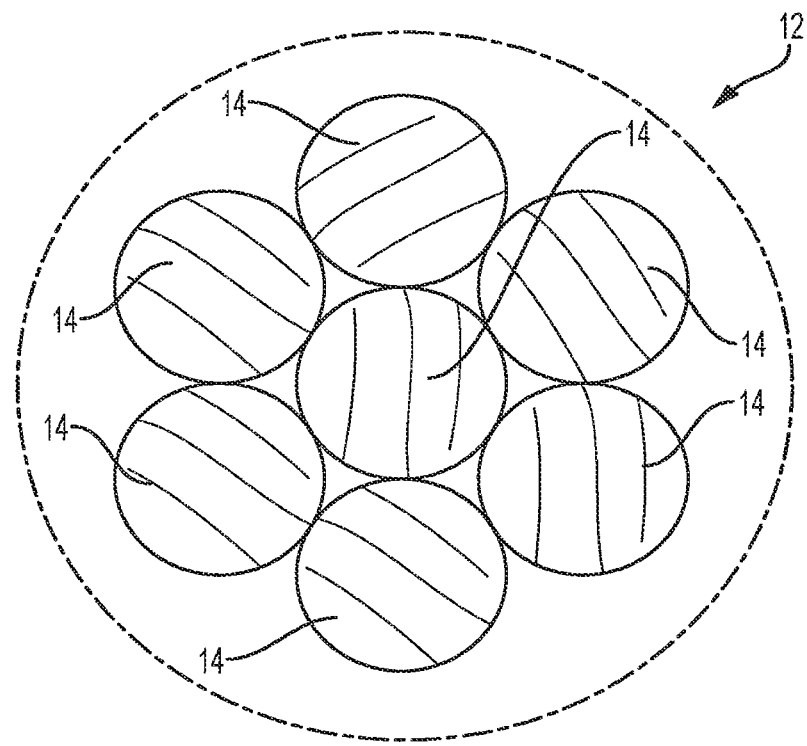
FIG. 8A is a cross-section, elevation view of a core and first layer of strand elements in the cable assembly of FIG. 6.
Figure 8B:
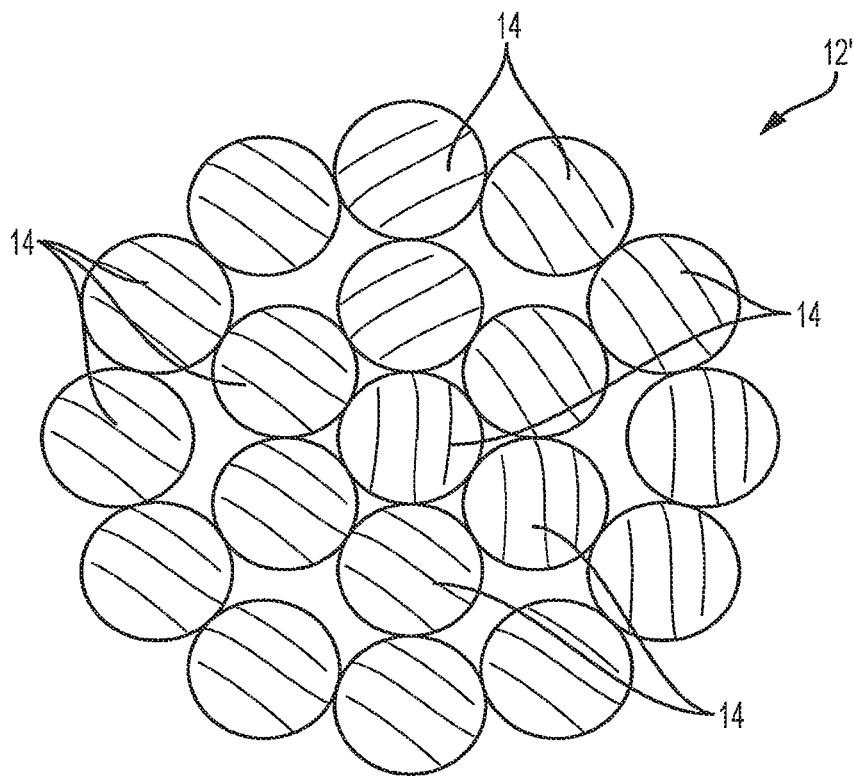
FIG. 8B is a cross-section, elevation view of a core and first and second layers of strand elements in the cable assembly of FIG. 6.
Figure 8C:
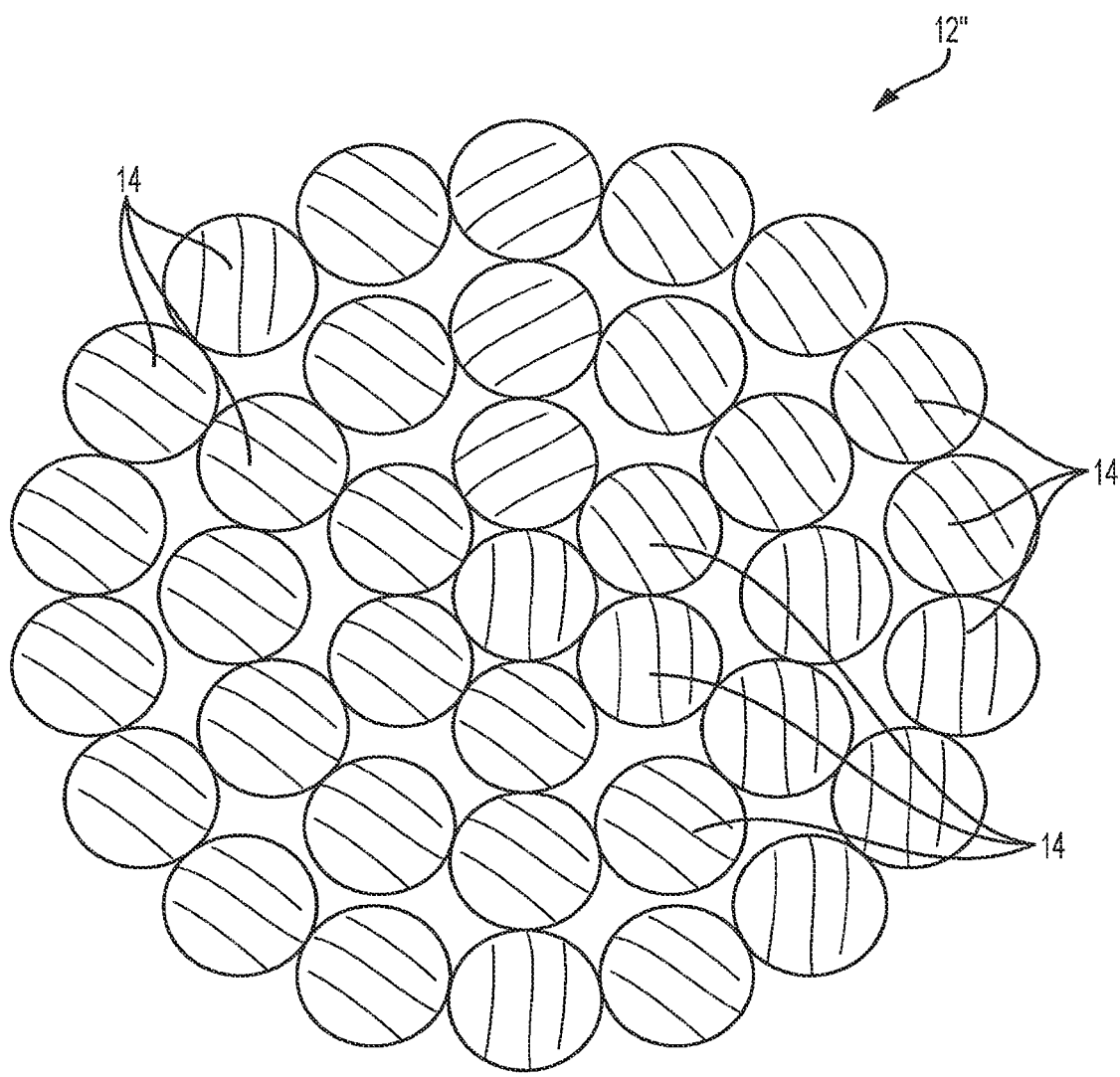
FIG. 8C is a cross-section, elevation view of a core and first, second and third layers of strand elements in the cable assembly of FIG. 6.

In one embodiment shown in FIG. 7, the strands 12 of the second, third, and fourth layers 18, 20 and 22 of cable 10 may be wound in alternating, sequentially opposite helical directions. For example, the strands 12 of second layer 18 may be wound in a first helical direction, the strands 12 of third layer 20 in a second, opposite helical direction, and the strands 12 of fourth layer 22 in the same helical direction as strands 12 of second layer 18.

Figure 4:
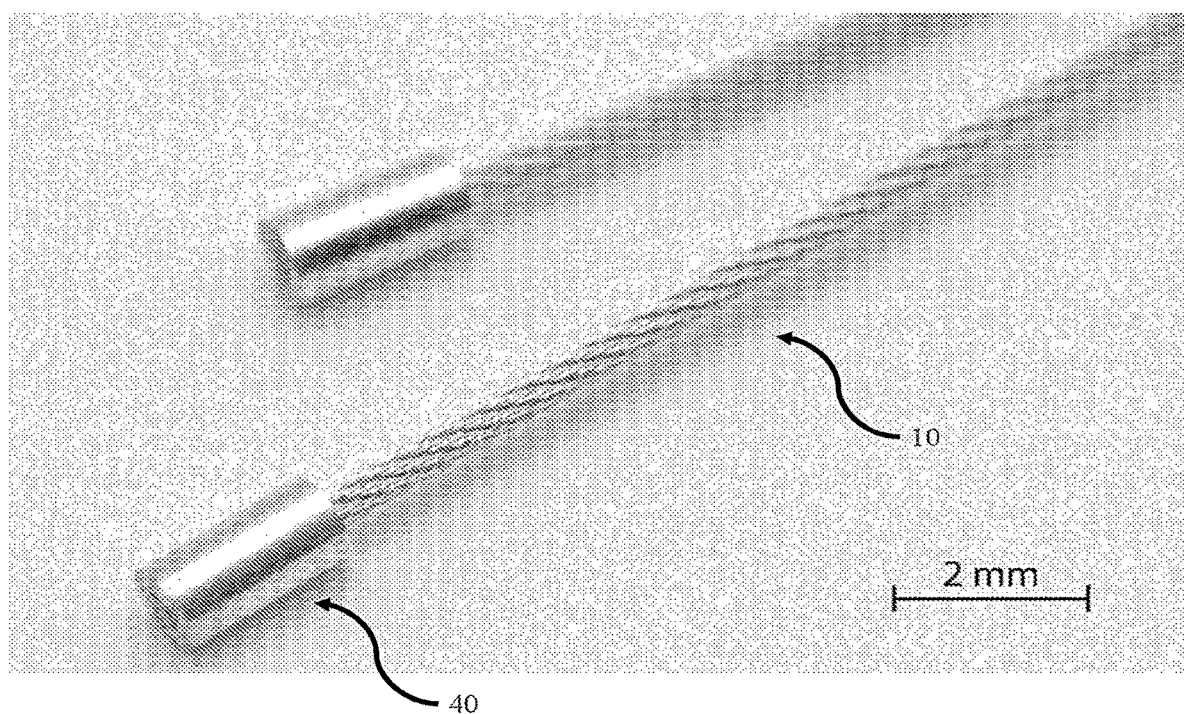
FIG. 4 is a perspective view of a pair of cables using a 7×7 construction with 50 μm filaments, to create a 0.450 mm outside diameter cable construction with swaged fittings, shown to scale in the focal plane according to the 2 mm scale at lower right.

FIG. 4 shows a 7×7 cable 10 utilizing filaments 14 made from wire 103 having an outer diameter of 50 μm, for a total cable outer diameter of 0.45 mm. UHS wires made in accordance with the present disclosure may be used for the individual filaments in wound cable strands 12, which are themselves wound into cable constructions. The resulting UHS cable 100 may therefore be made with wires 103 having ultimate strength levels greater than 5 GPa which translates to excellent cable performance.

For example, cable 100 of FIG. 4 utilizes 49 filaments 14 each made in accordance with the present disclosure. The resulting cable construct maintains an outer diameter less than 0.5 mm, and achieves extremely high stiffness, low stretch, good surface hardness and an ultimate (break) load exceeding 425 N (103 lbf).

Many other designs ranging from 1×3 and 1×7 strands up through 7×7×7, 7×19, 19×7, 19×19, 19×37, 37×37, and 61×61 can also be constructed in accordance with the present disclosure. One exemplary construction is a 19×19 cable using wires 103 for filaments 14, with each filament 14 having an outer diameter of 0.001 inches and made of a W—Re or Mo—Re material in accordance with the present disclosure, for an overall cable diameter of 0.025 inches.

Strands 12 having sixty-one (61) wire filaments 14 may be used in any cable configuration to provide further reduction of wire diameter within cable 10 while maintaining the same final cable diameter. An example would be replacing a 7×37 cable with a 7×61 cable in which the monofilament wire has a 22% smaller diameter in the 7×61 configuration compared to the comparable 7×37 configuration. Complex rope constructs may be made using strands with 7, 19, 37 or 61 filaments 14 per strand 12, or any number of filaments defined within any range defined by any pair of the foregoing values.

Even further, cables 10 including strands 12 having between 91 and 127 filaments 14 per strands 12 are possible as finer diameter, higher strength monofilaments enable these constructions. A cable constructed using a 7 μm diameter wire 103, made in accordance with the present disclosure, in a 61×61 constructions would have a final diameter of 0.57 mm including 3721 monolithic filaments 14. Further, the ductility of the material may lend itself to swage compression, end-forming and fitting attachments, such as the end fitting 40 shown in FIG. 4. Such attachments may be made by mechanical deformation, allowing for optimal force transmission and positional control.

Figure 5:
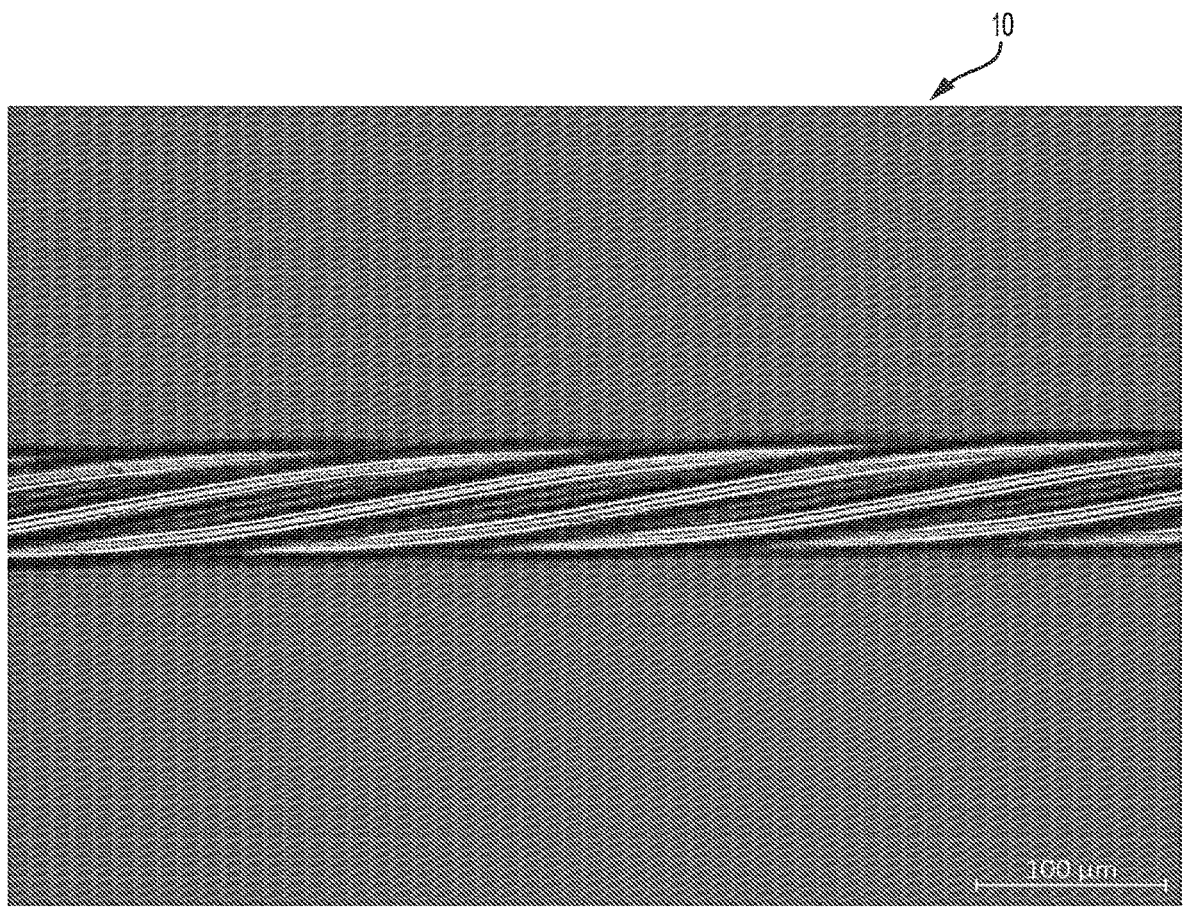
FIG. 5 is an elevation view of stranded wires using 25.4 μm Mo41Re wires drawn to an ultimate strength level of 5.6 GPa and then stranded into a 1×7 strand construction to 76 μm outside diameter, drawn to scale according to the 100 μm scale shown at lower right.
Figure 6:
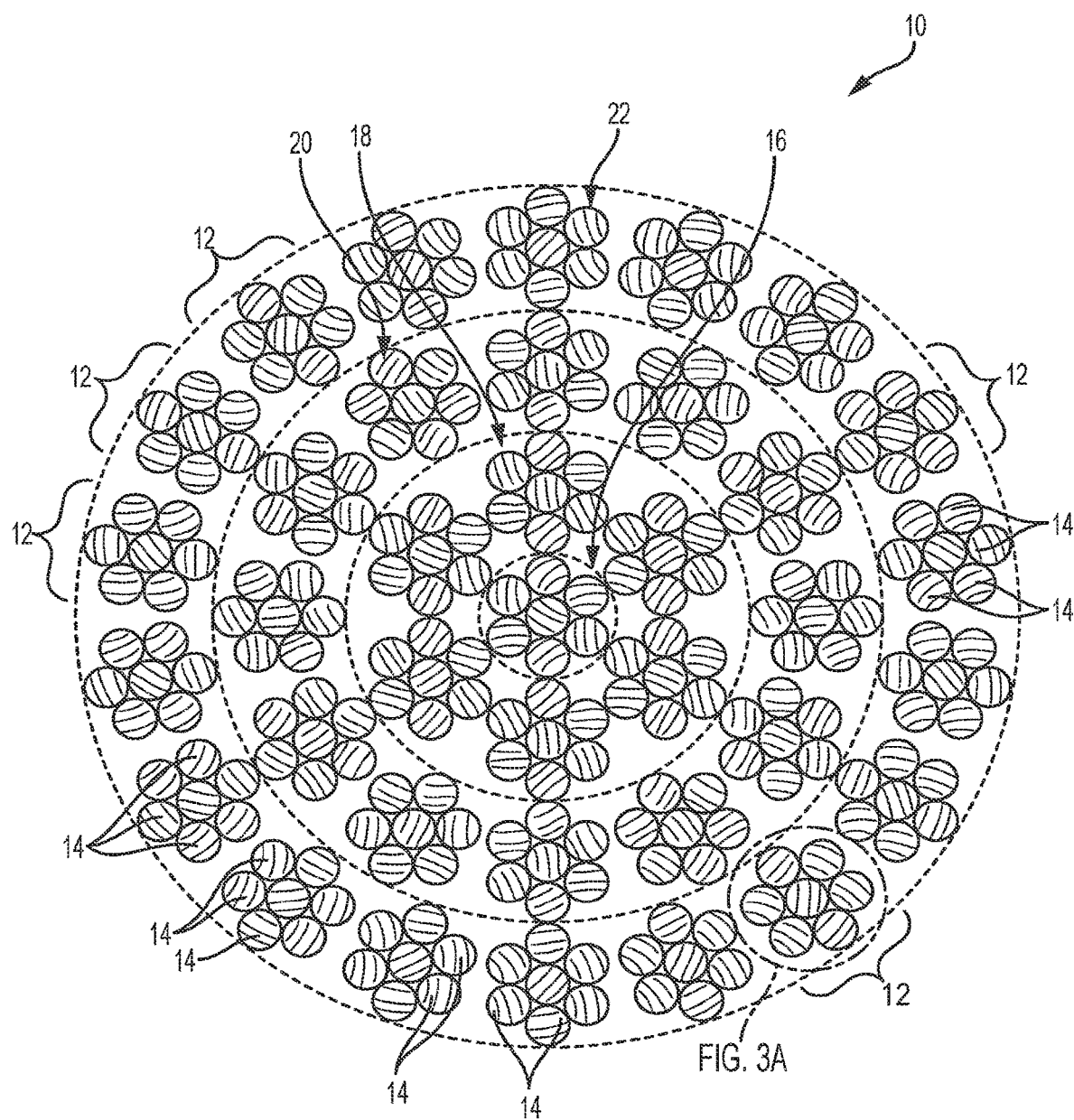
FIG. 6 is a cross-section, elevation view of a cable assembly.

In one exemplary embodiment shown in FIG. 5, a 1×7 construct can be used as a stand-alone cable 10, or as the constituent strands 12 for a larger cable construct. FIG. 5 is an elevation view of stranded wires 103 using 25.4 μm Mo41Re wires drawn to an ultimate strength level of 5.6 GPa and then stranded into a 1×7 strand construction. This produces a cable 10 (or strand 12) having a 76 μm outside diameter. This 1×7 construct exhibits a tensile strength of 5.4 GPa, very nearly matching the performance of the stand-alone monolithic wire 103. For purposes of the present disclosure, tensile strength of cables 10 (or strands 12) is determined based on the aggregated cross-sectional area of the filaments 14, not the cross-sectional area defined within the outer diameter of the cable 10 itself. This aggregated cross-sectional area may be referred to as the "solid area." Depending on the particular cable construct used, the solid area may be a lesser or greater percentage of the total cross-sectional area within the outer diameter of the cable 10. This percentage can be referred to as the "packing density" of the cable 10, a number which is greater than or equal to 54% for cables 10 made in accordance with the present disclosure. In constructs with more filaments 14, packing density increases and is a basic function of geometry which can be calculated by subtracting the aggregated total area of all filaments 14 from the area defined by the outer diameter of the cable 10, then dividing the difference be the area defined by the outer diameter of the cable 10.

In one exemplary embodiment, a cable 100 made in accordance with the present disclosure exhibits a low stretch of less than 0.02% cable-structural strain under a load of up to 3650 N/mm$^2$ of solid area packing density of at least 54%.

A set of exemplary cable constructs which may be made from the present materials in accordance with the present disclosure are shown in Table 1 below. In Table 1, the total number of filaments 14 is shown for each construct as "Wire Count." Assuming the filaments 14 share a common diameter in the resulting cable 100, "Multiplier (D)" shows the total outside diameter of the cable 100 as a function of the outer diameter of the constituent filaments 14. Thus, for a 1×3 construction, the outer diameter of the cable 100 is 2.15 times the outer diameter of the constituent filaments 14, while a 1×7 is 3 times, a 3×3 is 4.62 times, and so on.

TABLE 1

| Construction | Wire Count | Multiplier (D) |
|---|---|---|
| Monofilament | 1 | 1 |
| 1 × 3 | 3 | 2.15 |

TABLE 1-continued

| Construction | Wire Count | Multiplier (D) |
|---|---|---|
| 1 × 7 | 7 | 3 |
| 3 × 3 | 9 | 4.62 |
| 3 + 9 | 12 | 4.15 |
| 1 × 19 | 19 | 5 |
| 7 × 3 | 21 | 6.45 |
| 3 × 7 | 21 | 6.45 |
| 3 × 3 × 3 | 27 | 9.94 |
| 1 × 27 | 27 | 6.15 |
| 1 × 37 | 37 | 7 |
| 7 × 7 | 49 | 9 |
| 3 × 19 | 57 | 10.75 |
| 1 × 61 | 61 | 9 |
| 3 × 3 × 7 | 63 | 13.87 |
| 3 × 7 × 3 | 63 | 13.87 |
| 7 × 3 × 3 | 63 | 13.87 |
| 1 × 19 + (8) 1 × 7 | 75 | 11 |
| 7 × (3 + 9) | 84 | 12.45 |
| 7 × 19 | 133 | 15 |
| 19 × 7 | 133 | 15 |
| 7 × 3 × 7 | 147 | 19.35 |
| 7 × 7 × 3 | 147 | 19.35 |
| 7 × 27 | 189 | 18.45 |
| 7 × 7 + (8) 1 × 19 | 201 | 19 |
| 7 × 37 | 259 | 21 |
| 37 × 7 | 259 | 21 |
| 7 × 7 × 7 | 343 | 27 |
| 19 × 19 | 361 | 25 |
| 7 × 61 | 427 | 27 |
| 7 × 19 + (9) 1 × 37 | 466 | 29 |
| 19 × 27 | 513 | 30.75 |
| 7 × 7 × 12 | 588 | 37.4 |
| 19 × 37 | 703 | 35 |
| 37 × 19 | 703 | 35 |
| 7 × 7 × 19 | 931 | 45 |
| 37 × 27 | 999 | 43.05 |
| 19 × 61 | 1159 | 45 |
| 37 × 37 | 1369 | 49 |
| 61 × 27 | 1647 | 55.35 |
| 37 × 61 | 2257 | 63 |
| 61 × 61 | 3721 | 81 |

Additional details of cable construction and cables can be found in International Patent Application Publication No. WO2018/183862, filed Mar. 30, 2018 and entitled SMALL DIAMETER CABLE, the entire disclosure of which is hereby expressly incorporated herein by reference.

4. Drawing and Cold Work

For purposes of the present disclosure monolithic wire 103 (FIG. 9A) and composite wire 101 (FIG. 9B) may be considered interchangeable. For every instance of monolithic wire 103 being used as described herein (e.g., in a cable 10), composite wire 101 may be substituted for wire 103.

A W—Re or Mo—Re metal alloy in accordance with the present disclosure is first formed in bulk, such by casting an ingot, continuous casting, or extrusion of the desired material. This bulk material is then formed into a suitable intermediate, or pre-form, material (e.g., a rod, plate or hollow tube) by hot-working the bulk material into the desired pre-form size and shape. For purposes of the present disclosure, hot working is accomplished by heating the material to an elevated temperature above room temperature and performing desired shaping and forming operations while the material is maintained at the elevated temperature. A coarse wire structure is then made by, for example, a schedule of drawing and annealing the intermediate material to create a structure ready for final processing into wires 101 or 103. Thereafter, the coarse wire structure may be subjected to one or more additional draws, as well as a final cold work conditioning step (FIGS. 9A-9B) to form wires 101 or 103. One or more thermal processing steps such as shape setting, annealing and/or aging may then be performed in order to impart desired mechanical properties to the finished wire product, including strength and stiffness as discussed above. Further details of exemplary wire production and processing methods are further described below.

Figure 9B:
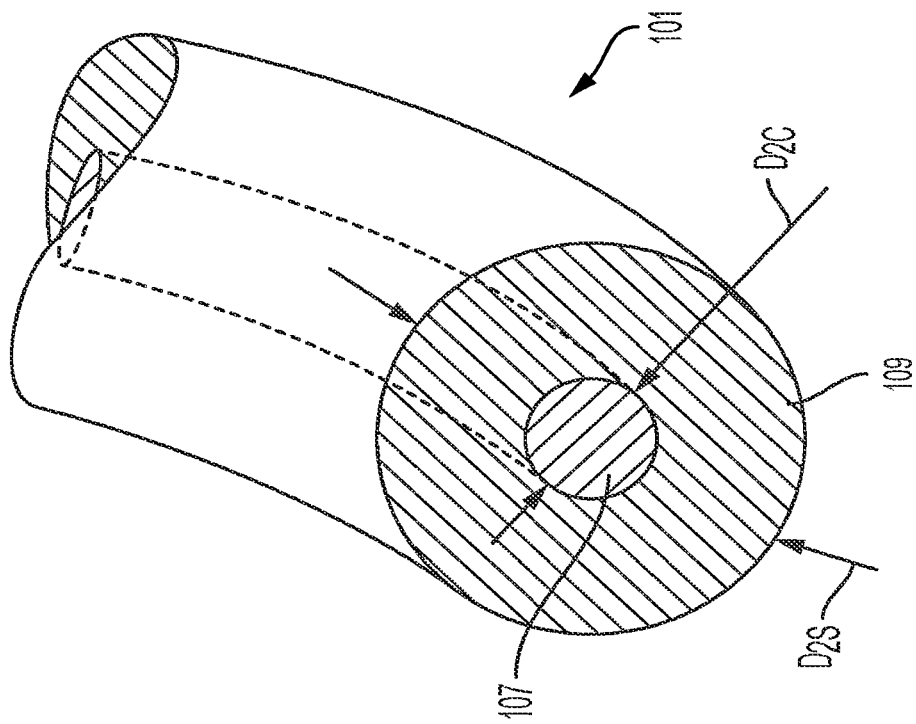
FIG. 9B is a cross-section, perspective view of a composite wire made in accordance with the present disclosure.
Figure 9A:
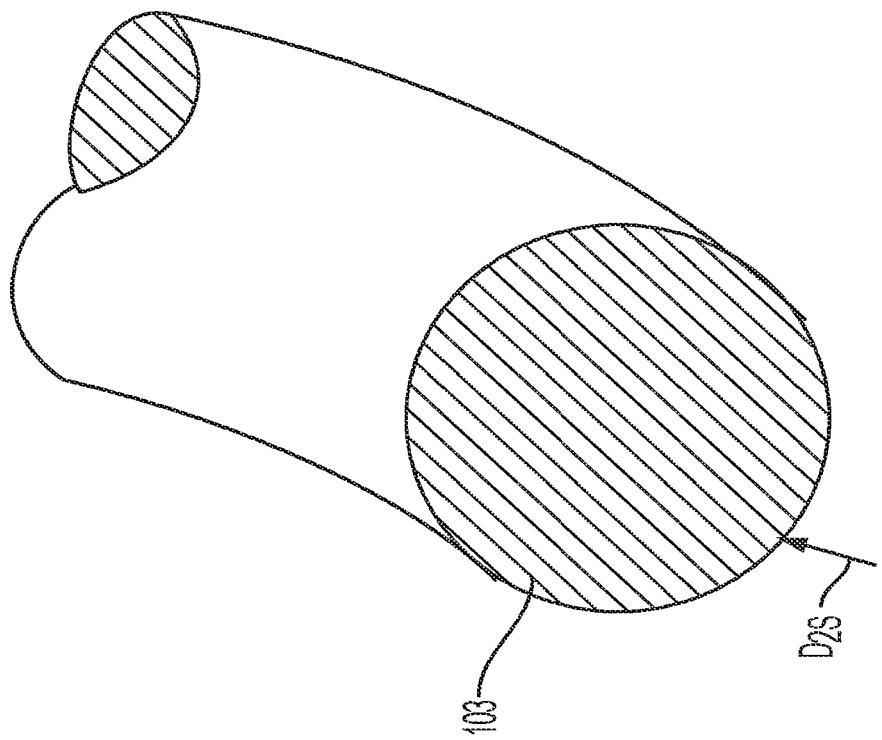
FIG. 9A is a cross-section, perspective view of a monolithic wire made in accordance with the present disclosure.

In one exemplary embodiment shown in FIG. 9A, monolithic wire 103 made of medical-grade metal material (described above) may be produced from a pre-form material into a wire of a desired diameter prior to final processing. That is, the pre-form material is drawn through one or more dies 105 (FIG. 10A) to reduce the outer diameter of the intermediate material slightly while also elongating the material, after which the material is annealed to relieve the internal stresses (i.e., retained cold work as discussed below) imparted to the material by the drawing process. This annealed material is then drawn through one or more new dies 105 with a smaller finish diameter to further reduce the diameter of the material, and to further elongate the material. Further annealing and drawing of the material is iteratively repeated until the material is formed into a drawn wire construct ready for final processing into wire 103.

Figure 10A:
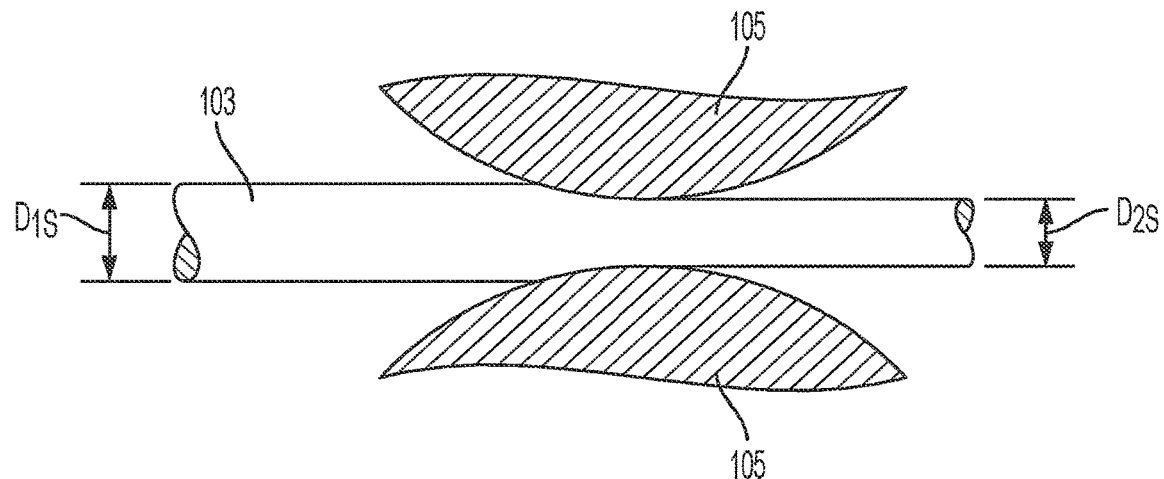
FIG. 10A is a schematic view illustrating an exemplary process of forming monolithic wire using a lubricated drawing die.
Figure 10B:
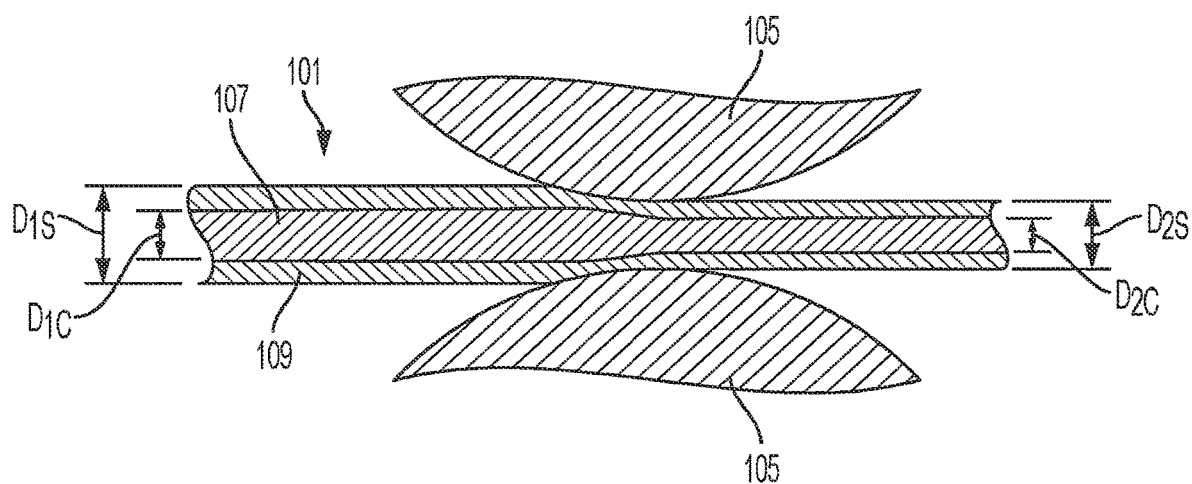
FIG. 10B is a schematic view illustrating an exemplary process of forming composite wire using a lubricated drawing die.

To form composite wire 101 (FIG. 9B), such as DFT® brand composite wire, core 107 is inserted within shell 109 to form an intermediate construct, and an end of this intermediate construct is then tapered to facilitate placement of the end into a first drawing die 105 (FIG. 10B). The end protruding through the drawing die 105 is then gripped and pulled through the die 105 to reduce the diameter of the construct and bring the inner surface of shell 109 into firm physical contact with the outer surface of core 107. More particularly, the initial drawing process reduces the inner diameter of shell 109, such that shell 109 closes upon the outer diameter of core 107 and the inner diameter of shell 109 equals the outer diameter of core 107. After this initial drawing, the inner core 107 completely fills the central cavity of the outer shell 109 when viewed in section, as shown in FIGS. 9B and 10B. Similar to monolithic wire 103 described above, this drawing process is then iteratively repeated to further reduce the diameter of the material, which also further elongates the material. Iterative annealing and drawing of the material is performed until the material is formed into a drawn wire construct ready for final processing into a drawn composite wire 101. Further detail regarding the construction and geometry of a composite wire in accordance with the present disclosure can be found in U.S. Pat. Nos. 7,420,124, 7,501,579 and 7,745,732, filed Sep. 13, 2004, Aug. 15, 2005 and Jan. 29, 2009 respectively and all entitled DRAWN STRAND FILLED TUBING WIRE, the entire disclosures of which are hereby expressly incorporated herein by reference.

Drawn wire constructs are structurally distinguished from constructs formed by other methods (e.g., casting, machining, coating, etc.) by their characteristic smoothness and high reflectivity. In the case of a bimetallic composite wire construct having a core and a shell, the circularity of the cross-section and the concentricity of the shell and core are substantially finer in a drawn construct as compared to, e.g., a coated construct. In addition, the microstructure of a drawn construct may be structurally distinct from other constructs, for example by exhibiting an elongated grain structure (shown in FIG. 2D and further discussed below) or a fine-grain structure after thermal processing.

Exemplary composite wires 101 may be formed using W—Re, and Mo—Re alloys in accordance with the present disclosure for either shell 109 or core 107. Other materials may be used in conjunction with the present materials as required or desired for a particular application.

The step of drawing subjects wire 101 or 103 to cold work. For purposes of the present disclosure, cold-working methods effect material deformation at or near room temperature, e.g. 20-30° C. In the case of composite wire 101, drawing imparts cold work to the material of both shell 109 and core 107, with concomitant reduction in the cross-sectional area of both materials. The total cold work imparted to wire 101 or 103 during a drawing step can be characterized by the following formula (I):

$$cw = 1 - \left(\frac{D_2}{D_1}\right)^2 \times 100\% \quad (I)$$

wherein "cw" is cold work defined by reduction of the original material area, "$D_2$" is the outer cross-sectional diameter of the wire (i.e., $D_{2S}$ for monolithic wire 103, and both $D_{2C}$ and $D_{2S}$ for composite wire 101) after the draw or draws, and "$D_1$" is the outer cross-sectional diameter of the wire (i.e., $D_{1S}$ for monolithic wire 103, and both $D_{1C}$ and $D_{1S}$ for composite wire 101) prior to the same draw or draws.

Referring to FIGS. 10A and 10B, the cold work step may be performed by the illustrated drawing process. As shown, wire 101 or 103 is drawn through a lubricated die 105 having an output diameter $D_{2S}$, which is less than diameter $D_{1S}$ of wire 101 or 103 prior to the drawing step. The outer diameter of wire 101 or 103 is accordingly reduced from pre-drawing diameter $D_{1S}$ to drawn diameter $D_{2S}$, thereby imparting cold work cw.

Alternatively, net cold work may be accumulated in wire 101 or 103 by other processes such as cold-swaging, rolling the wire (e.g., into a flat ribbon or into other shapes), extrusion, bending, flow forming, pilgering or cold-forging. Cold work may also be imparted by any combination of techniques including the techniques described here, for example, cold-swaging followed by drawing through a lubricated die finished by cold rolling into a ribbon or sheet form or other shaped wire forms. In one exemplary embodiment, the cold work step by which the diameter of wire 101 or 103 is reduced from $D_{1S}$ to $D_{2S}$ is performed in a single draw and, in another embodiment, the cold work step by which the diameter of wire 101 or 103 is reduced from $D_{1S}$ to $D_{2S}$ is performed in multiple draws which are performed sequentially without any annealing step therebetween.

For processes where the drawing process is repeated without an intervening anneal on composite wire 101, each subsequent drawing step further reduces the cross section of wire 101 proportionately, such that the ratio of the sectional area of shell 109 and core 107 to the overall sectional area of wire 101 is nominally preserved as the overall sectional area of wire 101 is reduced. Referring to FIG. 10B, the ratio of pre-drawing core outer diameter $D_{1C}$ to pre-drawings shell outer diameter $D_{1S}$ is the same as the corresponding ratio post-drawing. Stated another way, $D_{1C}/D_{1S}=D_{2C}/D_{2S}$. Further details regarding wire drawing are discussed in U.S. patent application Ser. No. 12/395,090, filed Feb. 27, 2009, entitled "Alternating Core Composite Wire", assigned to the assignee of the present invention, the entire disclosure of which is incorporated by reference herein.

5. Annealing

Thermal stress relieving, otherwise known in the art as annealing, is achieved by heating the material to a nominal temperature not exceeding the melting point of the material or materials used in the construct. Annealing is used to improve the ductility of the construct between drawing steps, thereby allowing further plastic deformation by subsequent drawing steps. When calculating cold work cw using formula (I) above, it is assumed that no anneal has been performed subsequent to the process of imparting cold work to the material.

Heating wire 101 or 103 to a temperature sufficient to cause recrystallization of grains eliminates accumulated cold work. The cold work imparted by each iterative cold work process is relieved by fully annealing the material between draws, thereby enabling the next iterative cold working process for materials which might otherwise become brittle by repeated draws or other cold work processing. In full annealing, the cold-worked material is heated to a temperature sufficient to substantially fully relieve the internal stresses stored in the material, thereby relieving the stored cold work and "resetting" cold work to zero.

Figure 10C:
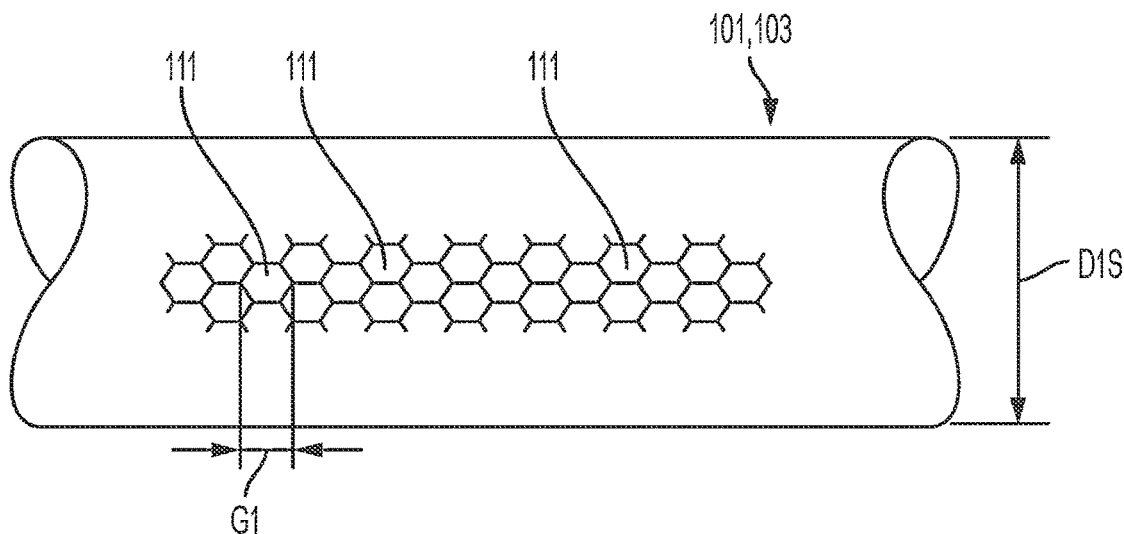
FIG. 10C is an elevation view of a wire in accordance with the present disclosure, before a final cold working process.
Figure 10D:
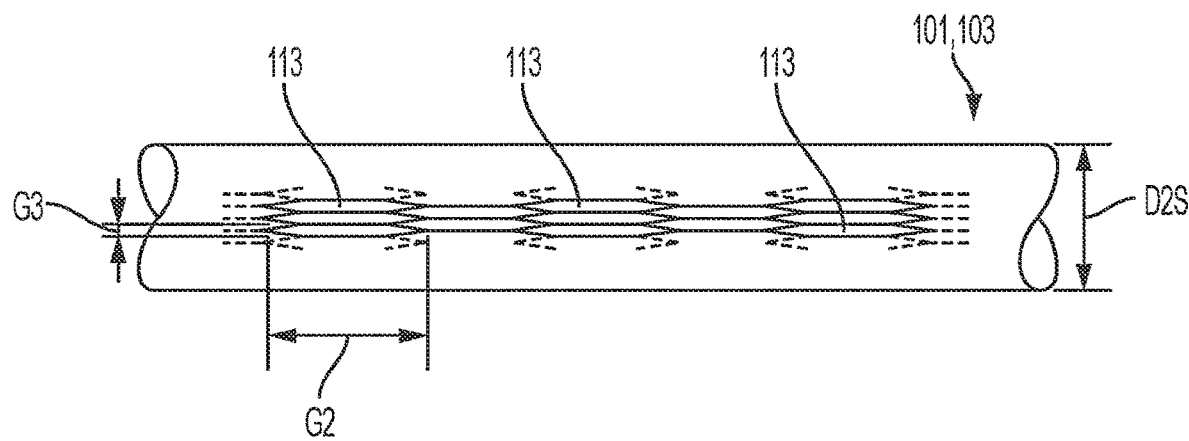
FIG. 10D is an elevation view of the wire of FIG. 10C, after the final cold working process.

On the other hand, wires 101 or 103 subject to drawing or other mechanical processing without a subsequent annealing process retain an amount of cold work. The amount of retained work depends upon the overall reduction in diameter from $D_{1S}$ to $D_{2S}$, and may be quantified on the basis of individual grain deformation within the material as a result of the cold work imparted. Referring to FIG. 10C, wire 103 is shown in a post-annealing state, with grains 111 shown substantially equiaxed, i.e., grains 111 define generally spheroid shapes in which a measurement of the overall length G1 of grain 111 is the same regardless of the direction of measurement. After drawing wire 101 or 103 (as described above), equiaxed grains 111 are converted into elongated grains 113 (FIG. 10D), such that grains 113 become longitudinal structures defining an elongated grain length G2 (i.e., the longest dimension across grain 113) and a relatively shorter grain width G3 (i.e., the shortest dimension across grain 113). The elongation of grains 113 results from the cold working process, with the longitudinal axis of grains 113 generally aligned with the direction of drawing, as illustrated in FIG. 10D.

The retained cold work of wire 101 or 103 after drawing can be expressed as the ratio of the elongated grain length G2 to the width G3, such that a larger ratio implies a grain which has been "stretched" farther and therefore implies a greater amount of retained cold work. By contrast, annealing wire 101 or 103 after an intermediate drawing process recrystallizes the material, converting elongated grains 113 back to equiaxed grains 111 and "resetting" the retained cold work ratio to 1:1 (i.e., no retained cold work).

For the above-described W—Re and Mo—Re alloys, full annealing or stress-relief annealing sufficient to tune strength and straightness properties may be accomplished at a temperature between 1400 to 2000 K a time dependent on the outer diameter $D_{2S}$ of wires 103, with higher temperatures associated with full annealing and lower temperatures associated with stress-relief annealing that does not fully recrystallize elongated grains 113 back to equiaxed grains 111. Annealing time, also called the "dwell time" during which the wire is exposed to the annealing temperature, is dependent on the size of the wire 103 and the desired effect of the annealing process, as well-understood by a person of skill in the art of material processing.

For purposes of the present discussion, annealing time may be assumed to be positively linearly correlated with the cross-sectional area of the wire being annealed. Thus, for a given annealing temperature, a similar annealing result is assumed for a first wire having a first cross-sectional area and annealed for a first amount of time, as for a second wire having twice the cross-sectional area of the first wire and annealed for a second amount of time that is twice the first time. However, for smaller fine wires and ultrafine wires, such as those having 200 μm or less, it may be assumed that the wire material becomes quickly heated through to the desired temperature, and the time for this heating is not significantly diameter-dependent. Thus, for wires 101 and 103 having diameters $D_{2S}$ less than 200 μm, the annealing time is not correlated to diameters $D_{2S}$ and is instead solely determined on the desired effect, i.e., full annealing or various gradations of stress-relief annealing as described above.

Moreover, annealing parameters can be expected to vary for varying wire diameters, with smaller diameters shortening the time of anneal for a given temperature and a given wire material. Whether a full anneal has been accomplished for any given wire sample can be verified in a number of ways as well known in the art, such as microstructural examinations using scanning electron microscopy (SEM), mechanical testing for ductility, strength, elasticity, etc., and other methods.

Further discussion of cold working and annealing methods can be found in U.S. Pat. No. 8,840,735, filed Sep. 18, 2009 and entitled FATIGUE DAMAGE RESISTANT WIRE AND METHOD OF PRODUCTION THEREOF, the entire disclosure of which is hereby incorporated by reference.

6. Applications

High tensile loaded strand, cable or rope-based tendons effecting distal tip actuation may benefit from use of wire constructs including the present UHS materials, such as W26Re, Mo41Re, and Mo47Re as discussed herein. Use of the present UHS materials delivers large durability performance gains compared to high strength stainless steel and tungsten constructs, with extended margins of safety with respect to material yielding and fatigue. Cables based on the present materials may provide any suitable mechanical function such as actuation, firing, release, manipulation, deflection, stabilization or any device where force transmission by use of a wire rope is desirable.

The combination of high strength, stiffness, ductility, and corrosion resistance allow the present materials to find use in other areas as well. For example, the present materials may be used in high strength braid for catheter or tube wall reinforcement, high stiffness and/or high strength vascular guide wires and neural embolic coil push wires with higher buckling tolerance, as well as high stiffness vascular stent architecture in both tubular-laser-cut or wire-based platforms to provide reduced wall thickness for a given chronic force requirement. The present UHS wires described herein offer 40-90% greater modulus of elasticity as compared to stainless steel and cobalt-chromium based constructs. Similar properties may also be imparted to well-processed thin wall tubing product.

Moreover, the UHS materials described herein offer roughly double the strength and stiffness of high strength stainless steel.

While this invention has been described as having exemplary designs, the present invention may be further modified with the spirit and scope of this disclosure. Further, this application is intended to cover such departures from the present disclosure as come within known or customary practice in the art to which this invention pertains.

What is claimed is:

1. A high strength cable construct comprising a plurality of drawn alloy filaments formed from a molybdenum-rhenium alloy, wherein the cable construct exhibits strength up to 4800 N/mm² of break load per solid cross-sectional filament area;
   wherein the plurality of filaments are formed from an alloy consisting of about 41 wt. % rhenium and balance molybdenum and inevitable impurities; and
   wherein each of the plurality of filaments has a diameter of between 7-12 μm and exhibits tensile strength up to 6.9 GPa.

2. The high strength cable construct of claim 1, wherein each of the plurality of filaments exhibits a 0.2% yield strength up to 6.2 GPa.

3. The high strength cable construct of claim 1, wherein each of the plurality of filaments exhibits a Young's elastic modulus up to 371 GPa.

4. The high strength cable construct of claim 1, wherein each of the plurality of filaments exhibits an engineering strain to fracture up to 2.3%.

5. The high strength cable construct of claim 1, wherein each of the plurality of filaments exhibits a work energy to fracture up to 99.6 mJ/mm³.

6. A high strength cable construct comprising a plurality of drawn alloy filaments formed from a molybdenum-rhenium alloy, wherein the cable construct exhibits strength up to 4800 N/mm² of break load per solid cross-sectional filament area;
   wherein the plurality of filaments are formed from an alloy consisting of about 41 wt. % rhenium and balance molybdenum and inevitable impurities; and
   wherein each of the plurality of filaments has a diameter of between 20-30 μm and exhibits a work-energy to fracture up to 120 mJ/mm³.

7. The high strength cable construct of claim 6, wherein each of the plurality of filaments exhibits a tensile strength up to 5.66 GPa.

8. The high strength cable construct of claim 6, wherein each of the plurality of filaments exhibits elongation to fracture up to 3% engineering strain.

9. The high strength cable construct of claim 6, wherein each of the plurality of filaments exhibits 0.2% yield strength up to 5.00 GP.

10. The high strength cable construct of claim 6, wherein each of the plurality of filaments exhibits Young's elastic modulus up to 370 GPa.

11. A high strength cable construct comprising a plurality of drawn alloy filaments formed from one of a tungsten-rhenium or a molybdenum-rhenium alloy, wherein the cable construct exhibits strength up to 4800 N/mm² of break load per solid cross-sectional filament area;
    wherein the plurality of filaments each have a diameter between 7-100 μm; and
    wherein the plurality of filaments comprises between 49 and 3721 filaments.

12. The high strength cable construct of claim 11, wherein between 9 and 81 wire diameters are required to traverse the overall cable diameter.

13. The high strength cable construct of claim 11, wherein each of the plurality of filaments exhibits strength up to 5500 N/mm².

14. The high strength cable construct of claim 11, wherein each of the plurality of filaments exhibits strength up to 6200 N/mm².

15. The high strength cable construct of claim 11, wherein each of the plurality of filaments exhibits a low stretch of less than 0.02 cable-structural strain under a load of up to 3650 N/mm² of solid area assuming a packing density of greater than or equal to 54%.

16. The high strength cable construct of claim 11, wherein each of the plurality of filaments exhibits fatigue durability up to 10 M cycles without fracture under alternating stress loads of 1000 N/mm².

17. The high strength cable construct of claim 11, wherein each of the plurality of filaments exhibits fatigue durability up to 10 M cycles without fracture under alternating stress loads of 1500 N/mm².

18. The high strength cable construct of claim 11, wherein each of the plurality of filaments exhibits fatigue durability up to 10M cycles without fracture under alternating stress loads of 2000 N/mm².

19. The high strength cable construct of claim 11, wherein each of the plurality of filaments exhibits a bright surface finish, or a smooth drawn oxide finish.

20. The high strength cable construct of claim 11, wherein each of the plurality of filaments includes a rhenium content ranging from 20 to 50 wt. %.

21. The high strength cable construct of claim 11, wherein the cable construct is used in combination with a surgical robot.

22. A high strength cable construct comprising a plurality of drawn alloy filaments formed from one of a tungsten-rhenium or a molybdenum-rhenium alloy, wherein the cable construct exhibits strength up to 4800 N/mm² of break load per solid cross-sectional filament area; and wherein the cable construct comprises 19 strands each having 19 of the plurality of filaments.

23. A high strength cable construct comprising a plurality of drawn alloy filaments formed from one of a tungsten-rhenium or a molybdenum-rhenium alloy, wherein the cable construct exhibits strength up to 4800 N/mm² of break load per solid cross-sectional filament area; and wherein each of the plurality of filaments has an outer diameter of about 0.001 inches, for an overall cable diameter of about 0.025 inches.

* * * * *